United States Patent [19]

Soll et al.

[11] Patent Number: 5,330,989

[45] Date of Patent: Jul. 19, 1994

[54] HETEROCYCLES SUBSTITUTED WITH BIPHENYL-3-CYCLOBUTENE-1,2-DIONE DERIVATIVES

[75] Inventors: Richard M. Soll, Lawrenceville, N.J.; William A. Kinney, Churchville, Pa.

[73] Assignee: American Home Products Corporation, Madison, N.J.

[21] Appl. No.: 943,614

[22] Filed: Sep. 11, 1992

Related U.S. Application Data

[63] Continuation-in-part of Ser. No. 782,029, Oct. 24, 1991, abandoned.

[51] Int. Cl.$^5$ .................. A61K 31/505; A01N 43/54; C07D 239/24; C07D 239/88
[52] U.S. Cl. .................... 514/258; 514/259; 514/260; 514/269; 514/272; 544/253; 544/285; 544/286; 544/291; 544/292; 544/293; 544/309; 544/310; 544/311; 544/312; 544/313; 544/314; 544/315; 544/316; 544/317; 544/318; 544/319; 544/321; 544/322; 544/323; 544/326; 544/330; 544/331; 544/332
[58] Field of Search ........................ 514/259, 260, 258; 544/285, 286, 287, 291, 292, 293, 253

[56] References Cited

U.S. PATENT DOCUMENTS 5,162,325  11/1992  Chakravarty et al. ............. 514/259
5,166,206  11/1992  Allen et al. ......................... 514/269

FOREIGN PATENT DOCUMENTS 419048  3/1992  European Pat. Off.

*Primary Examiner*—Mukund J. Shah
*Assistant Examiner*—Matthew V. Grumbling
*Attorney, Agent, or Firm*—Walter Patton

[57] ABSTRACT

Biphenyl derivatives of cyclobutene-1,2-dione of formula 1 are angiotensin II antagonists and are useful for the treatment of hypertension and congestive heart failure

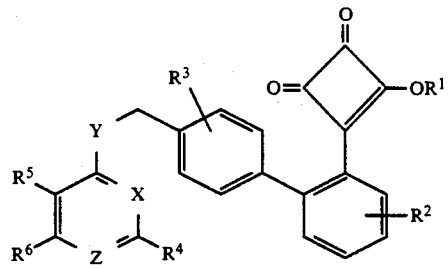

wherein:

Y is O, $NR^7$, $NCOR^7$; or $R^5$ and Y taken together represent a linking chain of $N=CR^8N$; or $R^5$ and Y taken together represent a linking chain of $(CR^9R^{10})_nCON$ where n=1,2,3,4, or 5;

X is N, $CR^7$;

Z is N, $CR^7$;

$R^1$ is H, alkyl, benzyl, alkoxyalkyl, phenyl;

$R^2$ is H, alkyl, benzyl, alkoxyalkyl, phenyl, alkoxy, alkyl-OH, perfluoroalkyl, F, Cl, Br, I, $NR^7R^8$;

$R^3$ is H, alkyl, benzyl, alkoxyalkyl, phenyl, alkoxy, alkyl-OH, perfluoroalkyl, F, Cl, Br, I, $NR^7R^8$;

$R^4$ is H, $NR^7R^8$, $OR^1$, CN, F, Cl, I, Br, perfluoroalkyl, alkyl, phenyl, alkoxy, alkyl-OH, alkoxyalkyl, $-(CH_2)_nCO_2R^1$, $-(CH_2)_nCONR^7R^8$ where n=1, 2, 3, 4, or 5;

$R^5$, $R^6$ is independently chosen from H, alkyl, benzyl, alkoxyalkyl, phenyl, F, Cl, $NR^7R^8$; or $R^5$ and $R^6$ taken together represent a linking chain of $CR^9R^{10}$ of up to 6 linking members; or $R^5$ and $R^6$ taken together represent a repeating linking chain of $(R^9C=CR^{10})$ up to 2 repeating units;

$R^7$ is H, alkyl, phenyl, benzyl;

$R^8$ is H, alkyl, phenyl, benzyl;

$R^9$ is chosen from H, alkyl, benzyl, alkoxyalkyl, phenyl, halogen, $OR^1$, $NR^7R^8$;

$R^{10}$ is chosen from H, alkyl, benzyl, alkoxyalkyl, phenyl, halogen, $OR^1$, $NR^7R^8$; wherein alkyl contains 1–8 branched or straight chain carbon atoms or the pharmaceutically acceptable sets thereof.

6 Claims, No Drawings

HETEROCYCLES SUBSTITUTED WITH BIPHENYL-3-CYCLOBUTENE-1,2-DIONE DERIVATIVES

This is a continuation-in-part application of copending application U.S. Ser. No. 07/782,029, filed Oct. 24, 1991, now abandoned.

BACKGROUND OF INVENTION

The compounds described in this invention as well as their non-toxic salts and pharmaceutical compositions containing them are useful for the treatment of hypertension and congestive heart failure. These compounds are also useful as lipid lowering agents.

The renin-angiotensin system plays a well-defined role in cardiovascular homeostasis [Ocain, T. D. et al. (1991) Drugs of the Future 16, 37–51]. Angiotensinogen is converted to angiotensin I by the enzyme renin. Angiotensin I is then acted upon by angiotensin converting enzyme (ACE) to form angiotensin II (A II). A II possesses many crucial properties including vasoconstriction, aldosterone release, and water retention and is implicated as the cause of high blood pressure in a number of species including man. These hypertensive responses are the result of A II acting at specific receptor sites. Compounds which are able to compete with A II for these receptor sites but do not elicit agonistic receptor responses can be expected to counteract (antagonize) the hypertensive effects of A II.

PRIOR ART

E. E. Allen et al describe 4-oxo-quinazolines in EP 0411766 A.

D. A. Roberts et al describe quinoline ethers in EP 0412848 A.

D. A. Roberts et al describe azabenzimidazoles in EP 0399731 A. Similarly, P. Chakravarty, et al describe azabenzimidazoles in EP 0400974 A.

D. J. Carini et al in U.S. Pat. No. 4,880,804 describe N-substituted benzimidaloles. P. Chakravarty et al disclose similar imidazole structures in EP 0401030 A where the phenyl aromatic ring is replaced by a seven membered heterocycle.

E. E. Allen et al disclose N-substituted oxopyrimidines in EP 0419048 A.

Similar structures are reported in EP 0424317 A by P. Herold et al.

Additionally, in all of the above prior art, the disclosures bear an aromatic ring possessing a tetrazoyl, carboxyl, phosphonyl, sulfonamide, carboxamide, N-sulfonyl, or N-carbonyl group.

The present invention differs from the above mentioned prior art in that it discloses non-peptidic substituted nitrogenous heterocyclic compounds which bear biphenyl derivatives of cyclobutene-1,2-dione.

DESCRIPTION OF THE INVENTION

The present invention describes the composition and utility of novel compounds of the general formula 1:

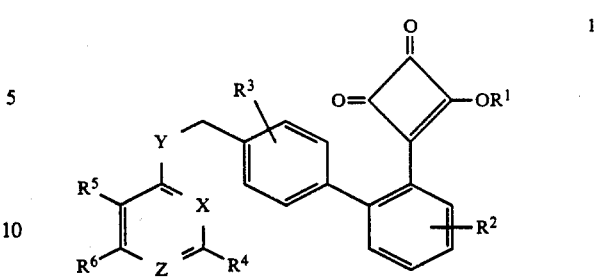

wherein:
Y is O, $NR^7$, $NCOR^7$; or $R^5$ and Y taken together represent a linking chain of $N=CR^8N$; or $R^5$ and Y taken together represent a linking chain of $(CR^9R^{10})_nCON$ where n=1, 2, 3, 4, or 5;
X is N, $CR^7$;
Z is N, $CR^7$;
$R^1$ is H, alkyl, benzyl, alkoxyalkyl, phenyl;
$R^2$ is H, alkyl, benzyl, alkoxyalkyl, phenyl, alkoxy, alkyl-OH, perfluoroalkyl, F, Cl, Br, I, $NR^7R^8$;
$R^3$ is H, alkyl, benzyl, alkoxyalkyl, phenyl, alkoxy, alkyl-OH, perfluoroalkyl, F, Cl, Br, I, $NR^7R^8$;
$R^4$ is H, $NR^7R^8$, $OR^1$, CN, F, Cl, I, Br, perfluoroalkyl, alkyl, phenyl, alkoxy, alkyl-OH, alkoxyalkyl, $-(CH_2)_nCO_2R^1$, $-(CH_2)_nCONR^7R^8$ where n=1, 2, 3, 4, or 5;
$R^5$, $R^6$ is independently chosen from H, alkyl, benzyl, alkoxyalkyl, phenyl, F, Cl, $NR^7R^8$; or $R^5$ and $R^6$ taken together represent a linking chain of $CR^9R^{10}$ of up to 6 linking members; or $R^5$ and $R^6$ taken together represent a repeating linking chain of $(R^9C=CR^{10})$ up to 2 repeating units;
$R^7$ is H, alkyl, phenyl, benzyl;
$R^8$ is H, alkyl, phenyl, benzyl;
$R^9$ is chosen from H, alkyl, benzyl, alkoxyalkyl, phenyl, halogen, $OR^1$, $NR^7R^8$;
$R^{10}$ is chosen from H, alkyl, benzyl, alkoxyalkyl, phenyl, halogen, $OR^1$, $NR^7R^8$; wherein alkyl contains 1–8 branched or straight chain carbon atoms or the pharmaceutically acceptable sets thereof.

More preferred compounds of of this invention are those of general formula 2:

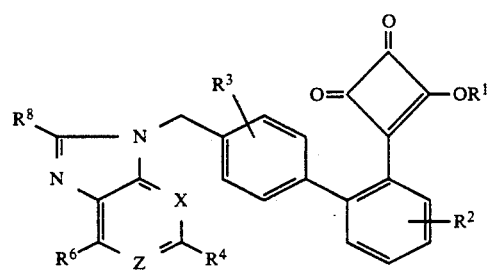

wherein:
X is N, $CR^7$;
Z is N, $CR^7$;
$R^1$ is H;
$R^2$ is H;
$R^3$ is H;
$R^4$ is H, alkyl, perfluoroalkyl;
$R^6$ is H, alkyl, perfluoroalkyl, halogen;
$R^7$ is H, alkyl, phenyl, benzyl;
$R^8$ is H, alkyl, phenyl, benzyl;

wherein alkyl contains 1-8 branched or straight chain carbon atoms or the pharmaceutically acceptable sets thereof.

More preferred compounds of of this invention are those of general formula 3:

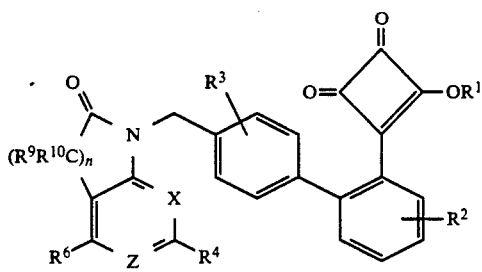

wherein:
where n=1, 2, 3, 4, or, 5;
X is N;
Z is N;
$R^1$ is H;
$R^2$ is H;
$R^3$ is H;
$R^4$ is H, alkyl, perfluoroalkyl;
$R^6$ is H, alkyl, perfluoroalkyl, halogen;
$R^9$ is chosen from H, alkyl, F;
$R^{10}$ is chosen from H, alkyl, F;
wherein alkyl contains 1-8 branched or straight chain carbon atoms or the pharmaceutically acceptable sets thereof.

More preferred compounds of of this invention are those of general formula 1:

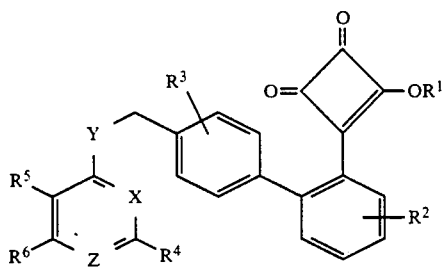

wherein:
Y is O, $NR^7$, $NCOR^7$;
X is N;
Z is N;
$R^1$ is H;
$R^2$ is H;
$R^3$ is H;
$R^4$ is H, perfluoroalkyl, alkyl, phenyl;
$R^5$, $R^6$ is independently chosen from H, alkyl, F; or $R^5$ and $R^6$ taken together represent a linking chain of $CR^9R^{10}$ of up to 6 linking members; or $R^5$ and $R^6$ taken together represent a repeating linking chain of ($R^9C=CR^{10}$) up to 2 repeating units;
$R^7$ is H, alkyl, phenyl;
$R^9$, $R^{10}$ is chosen independently from H, alkyl, F, phenyl;
wherein alkyl contains 1-8 branched or straight chain carbon atoms or the pharmaceutically acceptable sets thereof.

Still more preferred compounds of this invention are compounds of general formula 1 wherein:
Y is O, NH;
X is N;
Z is N;
$R^1$ is H;
$R^2$ is H;
$R^3$ is H;
$R^4$ is H, perfluoroalkyl, alkyl, phenyl;
$R^5$, $R^6$ is independently chosen from H, alkyl, F; or $R^5$ and $R^6$ taken together represent a linking chain of $CR^9R^{10}$ of up to 6 linking members;
$R^9$ is chosen from H, alkyl, phenyl, F;
$R^{10}$ is chosen from H, alkyl, phenyl, F;
wherein alkyl contains 1-8 branched or straight chain carbon atoms or the pharmaceutically acceptable sets thereof.

The most preferred compound of this invention is: 3-hydroxy-4-[4'-[[[5,6,7,8-tetrahydro-2-(trifluoromethyl)-4-quinazolinyl]amino]methyl][1,1'-biphenyl]-2-yl]-3-cyclobutene-1,2-dione or the pharmaceutically acceptable salt thereof.

PROCESS OF INVENTION

The compounds of general formula 1 can be prepared by standard procedures of organic chemistry well known in the art. For example, the compounds of formula 11 can be prepared as described in Scheme 1. The 4-chloroquinazoline 5 can be reacted with the aminomethylbiphenyl 4 (disclosed in EP 0323841) in the presence of a base such as sodium acetate, potassium carbonate or an organic base such as triethylamine in tetrahydrofuran, dioxane, dimethylformamide, dimethylsulfoxide or an alcohol at room temperature to reflux. Compound 6 may be reduced to aniline 7 using standard reducing conditions, such a catalytic hydrogenation over an activated palladium catalyst. Conversion of 7 to 8 may then be achieved through the standard Sandmeyer reaction or any variation therof. Cross coupling of 8 with 9 can be effected using the procedure of Liebeskind et. al. (J. Org. Chem. 1990, 55, 5359) under the influence of cocatalytic palladium catalyst (such as trans-benzyl(chloro)bis(triphenylphosphine)palladium-(II)) and Cu catalyst (such as copper (I) iodide). Hydrolysis can be effected by standard conditions, for example, heating in the presence of hydrochloric acid.

Extension to heterocyclic arrays defined by 1 are accomplished using similar sequences from 12,

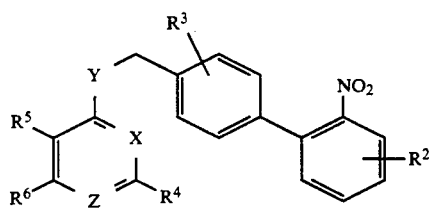

wherein $R^2$, $R^3$, $R^4$, $R^5$, $R^6$, X, Y, and Z are defined as above,
which is prepared by conventional procedures, for example in the case of imidazo-fused 6-membered heterocycles as described by P. chakravarty, et al in EP 0400974 A. Quinoline ether derivatives and azaindenes are prepared from 4'-(bromomethyl)-2-nitrobiphenyl (Carini et al, J. Med. Chem. 1991, 34, 2525) using analogous procedures described by Roberts et al in EP 0412848 A and EPA 399731. Similarly, pyrimidopyrimidines are prepared from 4 by procedures analogous to Sakamoto et al in *Chem. Pharm. Bull.* 1982, 30, 2410.

other modes of administration, for example parenteral administration for patients suffering from heart failure.

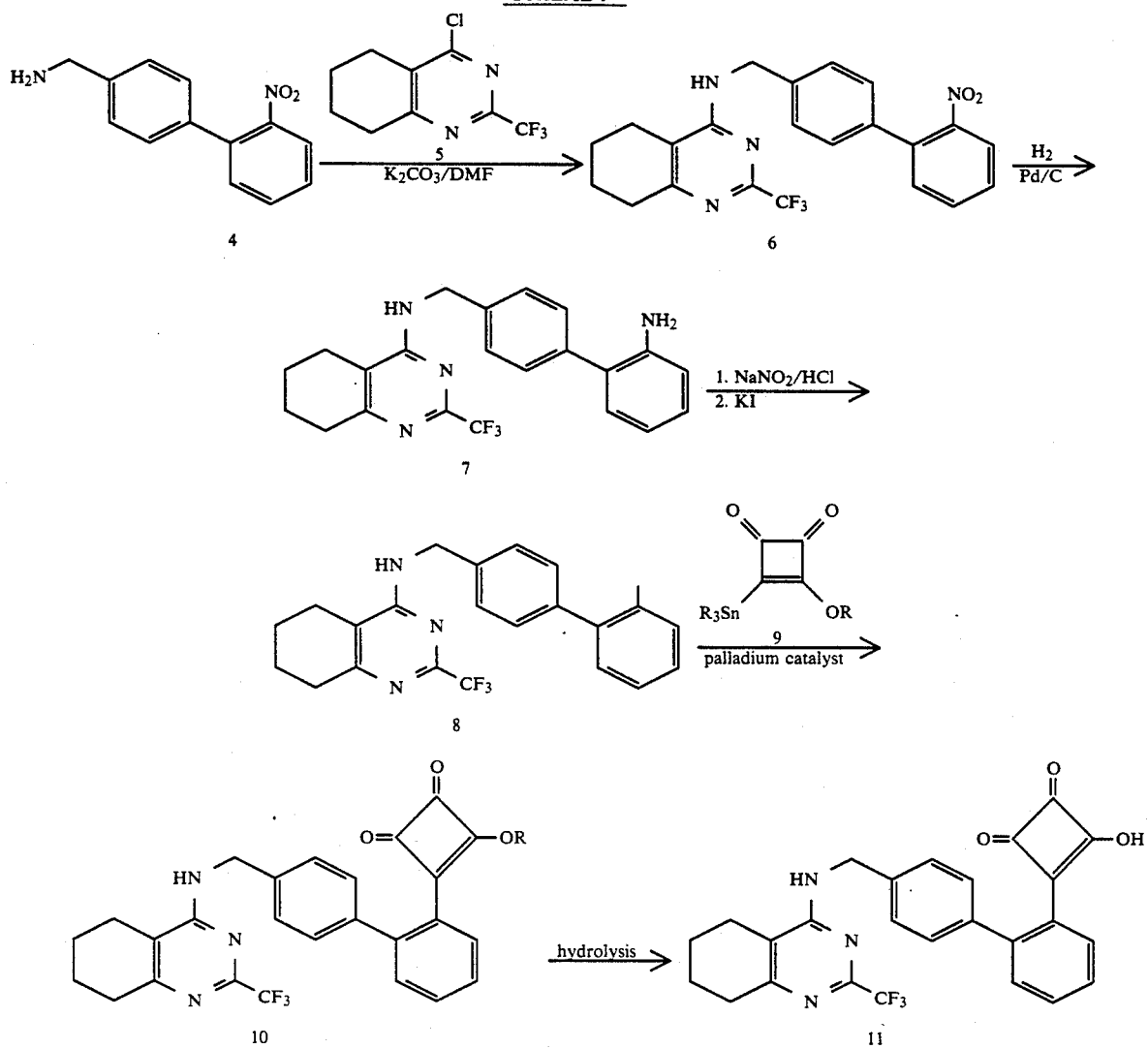

wherein R is phenyl or 1-8 branched or straight chain carbon atoms.

The compounds of this invention may also form salts with inorganic or organic bases. Any pharmaceutically acceptable salts of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, β-blocking agents or ACE inhibitors.

The present invention further provides a compound of the invention for use as an active therapeutic substance. Compounds described in this invention are of particular use in the treatment of hypertension. They can also be used for the treatment of congestive heart-failure. In addition, the compounds of this invention also have therapeutic utility in the treatment of hyperlipidemia, and/or hypercholesterolemia.

The present invention further provides a method of treating hypertension in mammals including man, which comprises administering to the afflicted mammal an antihypertensive effective amount of a compound or a pharmaceutical composition of the invention.

The high affinity of the compounds of this invention for the angiotensin II receptor was established using a rat adrenal receptor binding assay, measuring the displacement of radiolabeled angiotensin II from the receptor, described as follows: Anesthetize male Sprague-Dawley rats (300–400 g body weight) with $CO_2$ and sacrifice by cervical dislocation. Dissect adrenal glands and keep in ice-cold sucrose buffer (0.2M sucrose, 1 mM EDTA, 10 mM Trizma base, pH=7.2). Remove medulla by squashing. Mince the cortex, rinse and homogenize in a chilled ground glass tissue grinder with 15 mL sucrose buffer. Centrifuge at 3000×g for 10 min. (Sorvall RCSC centrifuge, SS34 rotor 6200 rpm). Decant supernatant through gauze. Centrifuge combined supernatants at 12000×g for 13 min. (Beckman ultracentrifuge, 80Ti rotor, 13000 rpm). Centrifuge the supernatant from the previous step at 102000×g for 60 min. (Beckman ultracentrifuge, 80Ti rotor, 38200 rpm). All steps are carried out at 4° C. Resuspend the pellet in 0.5 mL assay buffer (50 mM Tris HCl, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in 12×75 mm plastic test tubes or in 96-well plate (final volume of 0.25 mL). Add 140 μL assay buffer. Add 10 μL cold A II (to give final concentrations of $10^{-10}$–$10^{-7}$M for standard curve and $10^{-4}$M for nonspecific binding), compounds (e.g., for final concentrations of 25 and 100 μM or 1 μM, 10 nM and 100 nM) in 50% DMSO, or 50% DMSO as a control. Add 50 μL membrane suspension (e.g., 10 μg protein). Preincubate for 30 min at 25° C. Add 50 μl $^{125}$I-A II which has been prepared as shown below (final concentration=1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3× with 5 mL cold buffer (assay buffer without BSA). Cut and deposit the filter discs into test tubes and count on gamma counter for 1 min. Adjust the specific activity of $^{125}$I-A II purchased from New England Nuclear to 500 μCi/nmole by adding cold A II in water. Calculate the quantities of hot A II and the cold A II needed and make the dilution. Aliquot, seal tight, and store frozen until needed. Calculate the concentration of the total A II (hot+cold) after dilution. On the day of assay, thaw the frozen aliquot and adjust the volume to give a concentration of 5 pmole/mL (or 0.25 pmole/50 μL) with assay buffer (+protease-free BSA). For final concentration of 1 nM $^{125}$I-A II in the assay, add 50 μL (or 0.25 pmole) per test tube to a final volume of 250 μL. The results of these binding assays are reported as the inhibitory concentration of the test compound necessary to achieve fifty percent displacement of radiolabeled angiotensin II from its receptor ($IC_{50}$), or the present displacement of binding of A II at its receptor at $10^{-8}$M concentration of test compound (% I). The compound of Example 1 of this invention displayed an $IC_{50}$ in this assay of 25 nM.

In accordance with their ability to antagonize angiotensin II, the compounds of this invention show antihypertensive activity in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockage is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 μg/kg/min (at 9.6 μL/min). The A II infusion returns arterial pressure to or slightly above the control level. Once arterial pressure has stabilized with the A II infusion, baseline values for mean arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the compound of Example 1 administered at 3 mg/kg id lowered the A II dependent blood pressure by an average of 52% four hours post-administration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. These compounds will also be useful as antidepressants and anxiolytics and in the prevention or treatment of restenosis following angioplasty. The application of the compounds of this invention for these and similar disorders will be apparent to those skilled in the art.

Specific procedures are described in the following experimental example. This example is given to illustrate the invention and should not be construed as limiting the invention set forth in the appended claims.

EXPERIMENTAL

Example 1

The synthesis of 3-hydroxy-4-[4'-[[[5,6,7,8-tetrahydro-2-(trifluoromethyl)-4-quinzolinyl]amino]methyl][1,1'-biphenyl]-2-yl]-3-cyclobutene-1,2-dione.

Part A

A mixture of 2.56 g (11.2 mmol) of 2-(4'-aminomethylphenyl)nitrobenzene, 2.88 g (12.2 mmol) of 4-chloro-5,6,7,8-tetrahydro-2-trifluoromethylquinazoline, and 8.0 g (58 mmol) of potassium carbonate in DMF was stirred at 100° C. overnight. The reaction mixture was quenched with water and extracted into methylene chloride/tetrahydrofuran. The organic phase was washed with brine, dried over potassium carbonate, and purified by flash chromatography (elutions of ether/petroleum ether (1:2, then 1:1), then 10% ether/methylene chloride) to give 3.86 g (81%) of 5,6,7,8-tetrahydro-N-[(2'-nitro[1,1'-biphenyl]-4-yl)methyl]-2-(trifluoromethyl)-4-quinazolinamine, mp 150°–151° C.

NMR (CDCl$_3$, 400 MHz) δ 7.86 (d, 1H), 7.61 (dt, 1H), 7.48 (dt, 1H), 7.40–7.43 (m, 3H), 7.29 (d, 2H), 5.04 (bt, 1H), 4.78 (d, 1H), 2.78 (m, 2H), 2.35 (m, 2H), and 1.83–1.88 ppm (m, 4H)

MS (+CI): 429 (M+H)

Anal. Calcd. for $C_{22}H_{19}F_3N_4O_2$: C, 61.68; H, 4.47; N, 13.08. Found: C, 61.89; H, 4.45; N, 12.73.

Part B

A solution of 3.0 g (7 mmol) of 5,6,7,8-tetrahydro-N-[(2'-nitro[1,1'-biphenyl]-4-yl)methyl]-2-(trifluoromethyl)-4-quinazolinamine (prepared as described in Part A) in 100 mL of ethanol/tetrahydrofuran (1:1) was catalytically reduced with hydrogen (50 p.s.i. initial pressure) using 10% palladium on carbon. Upon completion, the reaction mixture was filtered through solka floc (tetrahydrofuran rinse) and concentrated to give 2.32 g (83%) of the product, 5,6,7,8-tetrahydro-N-[(2'-amino[1,1'-biphenyl]-4-yl)methyl]-2-(trifluoromethyl)-4-quinazolinamine, as a pale yellow foam which was used without further purification.

NMR (CDCl$_3$, 400 MHz) δ 7.43 (s, 4H), 7.14 (td, 1H), 7.09 (dd, 1H), 6.81 (td, 1H), 6.73 (dd, 1H), 5.02 (brt, 1H), 4.76 (d, 2H), 3.73 (brs, 2H), 2.78 (t, 2H), 2.34 (t, 2H), 1.80–1.89 ppm (m, 4H)

MS (+CI): 399 (M+H)

Anal. Calcd. for $C_{22}H_{21}F_3N_4$: C, 66.32; H, 5.31; N, 14.06. Found: C, 66.14; H, 5.33; N, 13.78.

Part C

At 0° C. to a solution of 1.7 g (4.27 mmol) of the product from Part B in 30 mL of acetonitrile was added 8 mL of 6N hydrochloric acid. Then 315 mg (4.56 mmol) of sodium nitrite was added. Water was then added to make the reaction mixture homogeneous. The reaction mixture was stirred at 0° C. for 20 min, then poured slowly into 12.7 g (77 mmol) of potassium iodide in 70 mL of water. After 30 min at ambient temperature, the reaction mixture was quenched with 2.5N sodium hydroxide (150 mL). The reaction mixture was then extracted into ether. The organic phase was washed with 2.5N NaOH, dried over potassium carbonate, and passed through a pad of silica gel (ether rinses). Concentration of the filtrate provided 1.98 g (91%) of the product, 5,6,7,8-tetrahydro-N-[(2'-iodo[1,1'-biphenyl]-4-yl)methyl]-2-(trifluoromethyl)-4-quinazolinamine, as a red foam which was used without further purification.

NMR (CDCl$_3$, 300 MHz) δ 7.95 (d, 1H), 7.2–7.5 (m, 7H), 5.06 (brt, 1H), 4.81 (d, 2H), 2.83 (br, 2H), 2.37 (br, 2H), and 1.87 ppm (m, 4H).

Part D

A solution of 1.7 g (3.35 mmol) of the product from Part C (5,6,7,8-tetrahydro-N-[(2'-iodo[1,1'-biphenyl]-4-yl)methyl]-2-(trifluoromethyl)-4-quinazolinamine), 2.0 g (4.66 mmol) of 4-(methylethoxy)-3-(tri-n-butylstannyl)cyclobut-3-ene-1,2-dione (Liebeskind and Feng, *J. Org. Chem.* 1990, 55, 5359), 250 mg (0.330 mmol) of trans-benzyl(chloro)bis(triphenylphosphine)palladium-(II), and 37 mg of copper(I) iodide in acetonitrile (70 mL) was heated at 70° C. for 90 min. An additional 170 mg (0.39 mmol) of 4-(methylethoxy)-3-(tri-n-butylstannyl)cyclobut-3-ene-1,2-dione was added. After stirring for another 60 min, the reaction mixture was quenched with water and extracted into ether. The organic phase was treated with 0.9 mL of 1,8-diazabicyclo[5.4.0]undec-7-ene. After stirring for 20 min, the reaction mixture was dried over magnesium sulfate and then filtered through a thick pad of silica gel (ether elution). The filtrate was concentrated and the product was purified by flash chromatography (ether/petroleum ether (4:1 to 8:1)) to give 1.5 g of a yellow foam. Re-flash chromatography (ether/petroleum ether (2:1, then 3:1)) provided 1.38 g (71% yield) of the product, 3-(1-methylethoxy)-4-[4'-[[[5,6,7,8-tetrahydro-2-(trifluoromethyl)-4-quinazolinyl]amino]methyl][1,1'-biphenyl]-2-yl]-3-cyclobutene-1,2-dione, as a yellow foam.

NMR (CDCl$_3$, 400 MHz) δ 7.99 (dd, 1H), 7.53 (td, 1H), 7.46 (td, 1H), 7.41 (dd, 1H), 7.37 (d, 2H), 7.26 (d, 1H), 5.22 (septet, 1H), 5.16 (br, 1H), 4.79 (d, 2H), 2.78 (brt, 2H), 2.36 (brt, 2H), 1.80–1.91 (m, 4H), and 1.02 ppm (d, 6H)

MS (+CI): 522 (M+H)

Anal. Calcd. for $C_{29}H_{26}F_3N_3O_4 \cdot 0.5\ H_2O$: C, 65.54; H, 5.14; N, 7.91. Found: C, 65.79; H, 5.00; N, 7.52.

Part E

A solution of 612 mg (1.17 mmol) of the product from Part D (3-(1-methylethoxy)-4-[4'-[[[5,6,7,8-tetrahydro-2-(trifluoromethyl)-4-quinazolinyl]amino]methyl][1,1'-biphenyl]-2-yl]-3-cyclobutene-1,2-dione) in tetrahydrofuran (10 mL) containing 3.5 mL of 6N hydrochloric acid was stirred at 45° C. overnight. The reaction mixture was concentrated to dryness and then azeotropically dried with toluene (3×100 mL). The residue was dissolved in tetrahydrofuran and then titurated with ether/petroleum ether to give 468 mg (83%) of a yellow powder. This product was dissolved in hot tetrahydrofuran/acetonitrile and then was triturated with ether/petroleum ether to give 3-hydroxy-4-[4'-[[[5,6,7,8-tetrahydro-2-(trifluoromethyl)-4-quinazolinyl]amino]methyl][1,1'-biphenyl]-2-yl]-3-cyclobutene-1,2-dione, mp 193° C. (dec., softening at 173° C.), as a yellow powder.

NMR (DMSO-d$_6$, 400 MHz) δ 7.82 (t, 1H), 7.64–7.67 (m, 1H), 7.3–7.4 (m, 3H), 4.63 (d, 2H), 2.63 (m, 2H), 2.49 (m, 2H), and 1.7–1.82 ppm (H, 4H)

MS (+FAB): 480 (M+H), 502 (M+Na), and 524 (M−H+2 Na)

Anal. Calcd. for $C_{26}H_{20}F_3N_3O_3 \cdot 0.5\ H_2O$: C, 63.93; N, 4.33; N, 8.60. Found: C, 63.99; H, 4.31; N, 8.60.

We claim:

1. The compounds of formula 1:

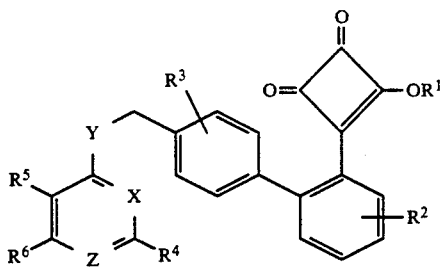

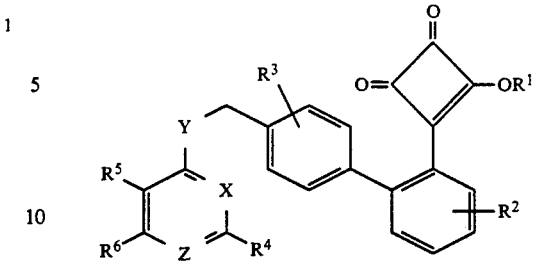

wherein:
Y is O, NR[7], or NCOR[7];
X is N;
Z is N;
R[1] is H, alkyl, benzyl, alkoxyalkyl, phenyl;
R[2] is H, alkyl, benzyl, alkoxyalkyl, phenyl, alkoxy, alkyl-OH, perfluoroalkyl, F, Cl, Br, I, NR[7]R[8];
R[3] is H, alkyl, benzyl, alkoxyalkyl, phenyl, alkoxy, alkyl-OH, perfluoroalkyl, F, Cl, Br, I, NR[7]R[8];
R[4] is H, NR[7]R[8], OR[1], CN, F, Cl, I, Br, perfluoroalkyl, alkyl, phenyl, alkoxy, alkyl-OH, alkoxyalkyl, —$(CH_2)_n CO_2 R^1$, —$(CH_2)_n CONR^7 R^8$ where n=1, 2, 3, 4, or 5;
R[5] and R[6] taken together represent a linking chain of CR[9]R[10] of 4 linking members; or R[5] and R[6] taken together represent a repeating linking chain of (R[9]C=CR[10]) up to 2 repeating units;
R[7] is H, alkyl, phenyl, benzyl;
R[8] is H, alkyl, phenyl, benzyl;
R[9] is chosen from H, alkyl, benzyl, alkoxyalkyl, phenyl, halogen, OR[1], NR[7]R[8];
R[10] is chosen from H, alkyl, benzyl, alkoxyalkyl, phenyl, halogen, OR[1], NR[7]R[8];
wherein alkyl contains 1-8 branched or straight chain carbon atoms or the pharmaceutically acceptable salts thereof.

2. The compounds of formula 1:

wherein:
Y is O, NR[7], NCOR[7];
X is N;
Z is N;
R[1] is H;
R[2] is H;
R[3] is H;
R[4] is H, perfluoroalkyl, alkyl, phenyl;
R[5] and R[6] taken together represent a linking chain of CR[9]R[10] of 4 linking members; or R[5] and R[6] taken together represent a repeating linking chain of (R[9]C=CR[10]) up to 2 repeating units;
R[7] is H, alkyl, phenyl;
R[9], R[10] is chosen independently from H, alkyl, F, phenyl;
wherein alkyl contains 1-8 branched or straight chain carbon atoms or the pharmaceutically acceptable salts thereof.

3. The compound 3-hydroxy-4-[4'-[[[5,6,7,8-tetrahydro-2-(trifluoromethyl)-4-quinazolinyl]amino]methyl][1,1'-biphenyl]-2-yl]-3-cyclobutene-1,2-dione or the pharmaceutically acceptable salt thereof.

4. A pharmaceutical composition containing a compound of claim 1, in an amount effective for producing a hypotensive response in a mammal, and a pharmaceutically acceptable carrier, vehicle or diluent.

5. A method for lowering blood pressure in a mammal by administering to that mammal a compound of claim 1 in a hypotensively effective amount.

6. A method for preventing or treating restenosis following angioplasty in a mammal by administering to that mammal an effective amount of a compound in claim 1.

* * * * *